(12) United States Patent
Kim et al.

(10) Patent No.: US 9,527,879 B2
(45) Date of Patent: Dec. 27, 2016

(54) ASTER GLEHNI EXTRACTS, FRACTIONS OR COMPOUNDS ISOLATED THEREFROM FOR THE TREATMENT OR PREVENTION OF HYPERURICEMIA OR GOUT

(71) Applicant: KOREA INSTITUTE OF SCIENCE AND TECHNOLOGY, Seoul (KR)

(72) Inventors: Hyoung Ja Kim, Seoul (KR); Chang Bae Jin, Seoul (KR); Min Jeoung Son, Seoul (KR); Yong Sup Lee, Seoul (KR); Chang Soo Yook, Seoul (KR); Jae Yeol Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/717,016

(22) Filed: May 20, 2015

(65) Prior Publication Data

US 2015/0337001 A1 Nov. 26, 2015

(30) Foreign Application Priority Data

May 23, 2014 (KR) .......................... 10-2014-0062501
Sep. 12, 2014 (KR) .......................... 10-2014-0121178

(51) Int. Cl.
| | |
|---|---|
| *A61K 36/00* | (2006.01) |
| *C07H 15/207* | (2006.01) |
| *A61K 36/28* | (2006.01) |
| *C07H 15/10* | (2006.01) |
| *C07H 15/18* | (2006.01) |
| *A61K 31/704* | (2006.01) |

(52) U.S. Cl.
CPC ........... *C07H 15/207* (2013.01); *A23L 33/105* (2016.08); *A61K 31/704* (2013.01); *A61K 36/28* (2013.01); *C07H 15/10* (2013.01); *C07H 15/18* (2013.01); *A61K 2236/00* (2013.01)

(58) Field of Classification Search
None
See application file for complete search history.

(56) References Cited

FOREIGN PATENT DOCUMENTS

| KR | 10-2012-0067183 A | 6/2012 |
| KR | 20120067183 A * | 6/2012 |
| KR | 10-2013-0044286 A | 5/2013 |

OTHER PUBLICATIONS

Kim et al.,"Anti-oxidant and anti-inflammation Activity of Fractions from Aster glehni Fr.Schm.", Kor. J. Microbiol. Biotechnol., 2010, pp. 434-441, vol. 38 No. 4, Republic of Korea.
Kim et al.,"The Extract of *Aster glehni* Leaves Rich in Caffeoylquinic Acids Prevents Atherogenic Index, Oxidative Stress, and Body Weight Increase in High-Fat Diet-Induced Rats", Korean Journal of Pharmacognosy, 2011, pp. 54-60, vol. 42(1), Republic of Korea.

* cited by examiner

*Primary Examiner* — Qiuwen Mi
(74) *Attorney, Agent, or Firm* — Goldilocks Zone IP Law

(57) ABSTRACT

The present invention relates to an *Aster glehni* extract, a fraction thereof and the active compounds isolated therefrom, which are effective for the treatment, prevention and improvement of hyperuricemia or gout. The *Aster glehni* extract, the fraction thereof and 6'-O-caffeoylampelopsisionoside, 6'-O-caffeoylroseoside, 6'-O-caffeoylsonchuinoside C, 6'-O-caffeoyldihydrosyringin and glehnoside as the active compounds isolated from the fraction according to the present invention have substantial effect of inhibiting production of uric acid and decreasing its concentration. Accordingly, the *Aster glehni* extract, the fraction thereof and the active compounds isolated therefrom the fraction according to the present invention can be effectively used as an active ingredient of a drug, health food, etc. for the treatment, prevention and improvement of such as hyperuricemia or gout, which are diseases induced by increased level of uric acid.

7 Claims, 11 Drawing Sheets

ASTER GLEHNI EXTRACTS, FRACTIONS OR COMPOUNDS ISOLATED THEREFROM FOR THE TREATMENT OR PREVENTION OF HYPERURICEMIA OR GOUT

CROSS-REFERENCE TO RELATED APPLICATIONS

This application claims priorities under 35 U.S.C. §119 to Korean Patent Applications Nos. 10-2014-0062501 and 10-2014-0121178, filed on May 23, 2014 and Sep. 12, 2014, in the Korean Intellectual Property Office, the disclosure of which is incorporated herein by reference in its entirety.

BACKGROUND (a) Technical Field

The present invention relates to an *Aster glehni* extract, fractions thereof and the active compounds isolated therefrom, which are effective for the treatment, prevention and improvement of hyperuricemia or gout.

(b) Background Art

Hyperuricemia or gout is induced as the intake of uric acid increases due to westernized diet and the uric acid is not normally degraded in the body. The incidence of hyperuricemia or gout is increasing gradually as the intake of alcohols, animal viscera and seafood increases. It is reported that hyperuricemia or gout can increase the incidence of hypertension, hyperlipidemia, cancer, diabetes, obesity, etc.

Gout occurs frequently in men in their 40s to 50s. However, due to the recent change in diet, the age of prevalence is gradually decreasing. It can occur easily in those who take immunosuppressants for a long time after organ transplantation, those who take diuretics for a long time and women of childbearing age. The currently used drugs for treating gout, allopurinol, benzbromarone, sulfinpyrazone and probenecid, were developed in 1950s and 1960s. Among these, allopurinol is the best known drug for gout treatment but there are concerns about hypersensitivity syndrome, which can be lethal, in addition to interstitial nephritis, renal disorder, hepatotoxicity, vasculitis and skin rash. Although benzbromarone is the most potent drug clinically used in the treatment of gout, its use is restricted because of severe hepatotoxicity. Although sulfinpyrazone and probenecid have been used until recently, they are known to cause renal failure.

As described above, it is thought that the direct cause of gout is the increase in uric acid. Therefore, the inventors of the present invention have researched to develop a drug of natural origin for treating gout, which is substantially effective in decreasing uric acid.

While searching for various natural products to develop a drug that exhibits potent effect of reducing uric acid, the inventors of the present invention have found out that *Aster glehni* has remarkable antiinflammatory, anticonvulsant, sedative or sleep-inducing effects. The excellent uric acid decreasing effect of *Aster glehni* has never been reported.

REFERENCES OF THE RELATED ART

Patent Documents (Patent document 1) Korean Patent No. 1,333,982, "Sedative or sleep-inducing pharmaceutical composition comprising *Aster glehni* extract as active ingredient".

(Patent document 2) Korean Patent No. 1,382,099, "Anticonvulsant composition comprising *Aster glehni* extract, fraction thereof or compound isolated therefrom".

Non-Patent Documents (Non-patent document 1) "Antioxidant and antiinflammatory activities of fractions from *Aster glehni*", *Kor. J. Microbiol. Biotechnol.*, 2010, 38, 434.

(Non-patent document 2) "The Extract of *Aster glehni* Leaves Rich in Caffeoylquinic Acids Prevents Atherogenic Index, Oxidative Stress, and Body Weight Increase in High-Fat Diet-Induced Rats", *Korean Journal of Pharmacognosy*, 2011, 42, 54.

SUMMARY

The present invention is directed to providing a composition for treating, preventing and improving hyperuricemia or gout, which contains an *Aster glehni* extract, fractions thereof or specific active compounds isolated therefrom as an active ingredient.

The present invention is also directed to providing a method for isolating the active compounds effective in decreasing the serum uric acid level from *Aster glehni*.

The present invention is also directed to providing the active compound as novel compounds.

In an aspect, the present invention provides a pharmaceutical composition or a health food composition for treating, preventing and improving hyperuricemia or gout, which contains an *Aster glehni* extract or fractions thereof.

In another aspect, the present invention provides a pharmaceutical composition or a health food composition for treating, preventing and improving hyperuricemia or gout, which contains one or more compound selected from a group consisting of 6'-O-caffeoylampelopsisionoside, 6'-O-caffeoylroseoside, 6'-O-caffeoylsonchuinoside C, 6'-O-caffeoyldihydrosyringin and glehnoside or a pharmaceutically acceptable salt, hydrate or solvate thereof.

In another aspect, the present invention provides a method for isolating the active compounds effective in decreasing the serum uric acid level from *Aster glehni*, which includes: 1) obtaining a solvent extract by extracting the aerial part or underground part of *Aster glehni* with one or more extraction solvent selected from dichloromethane, acetone, an aqueous solution of acetone, a $C_{1-4}$ alcohol and an aqueous solution of a $C_{1-4}$ alcohol; 2) obtaining an ethyl acetate fraction by extracting the solvent extract with water and ethyl acetate; and 3) obtaining 6'-O-caffeoylampelopsisionoside, 6'-O-caffeoylroseoside, 6'-O-caffeoylsonchuinoside C, 6'-O-caffeoyldihydrosyringin and glehnoside by subjecting the ethyl acetate fraction to column chromatography.

In another aspect, the present invention provides 6'-O-caffeoylampelopsisionoside, 6'-O-caffeoylroseoside, 6'-O-caffeoylsonchuinoside C, 6'-O-caffeoyldihydrosyringin and glehnoside as novel compounds.

The *Aster glehni* extract, the fraction thereof and the active compounds isolated therefrom according to the present invention are remarkably effective in reducing the serum uric acid level.

Accordingly, the *Aster glehni* extract, the fraction thereof and the active compounds isolated therefrom according to the present invention can be effectively used as an active ingredient to prepare a drug, health food, etc. for the treatment, prevention and improvement of hyperuricemia or gout.

Specifically, the gout may include gouty arthritis, gouty renal disease and gouty nephrolithiasis.

DETAILED DESCRIPTION

Figure 1A:
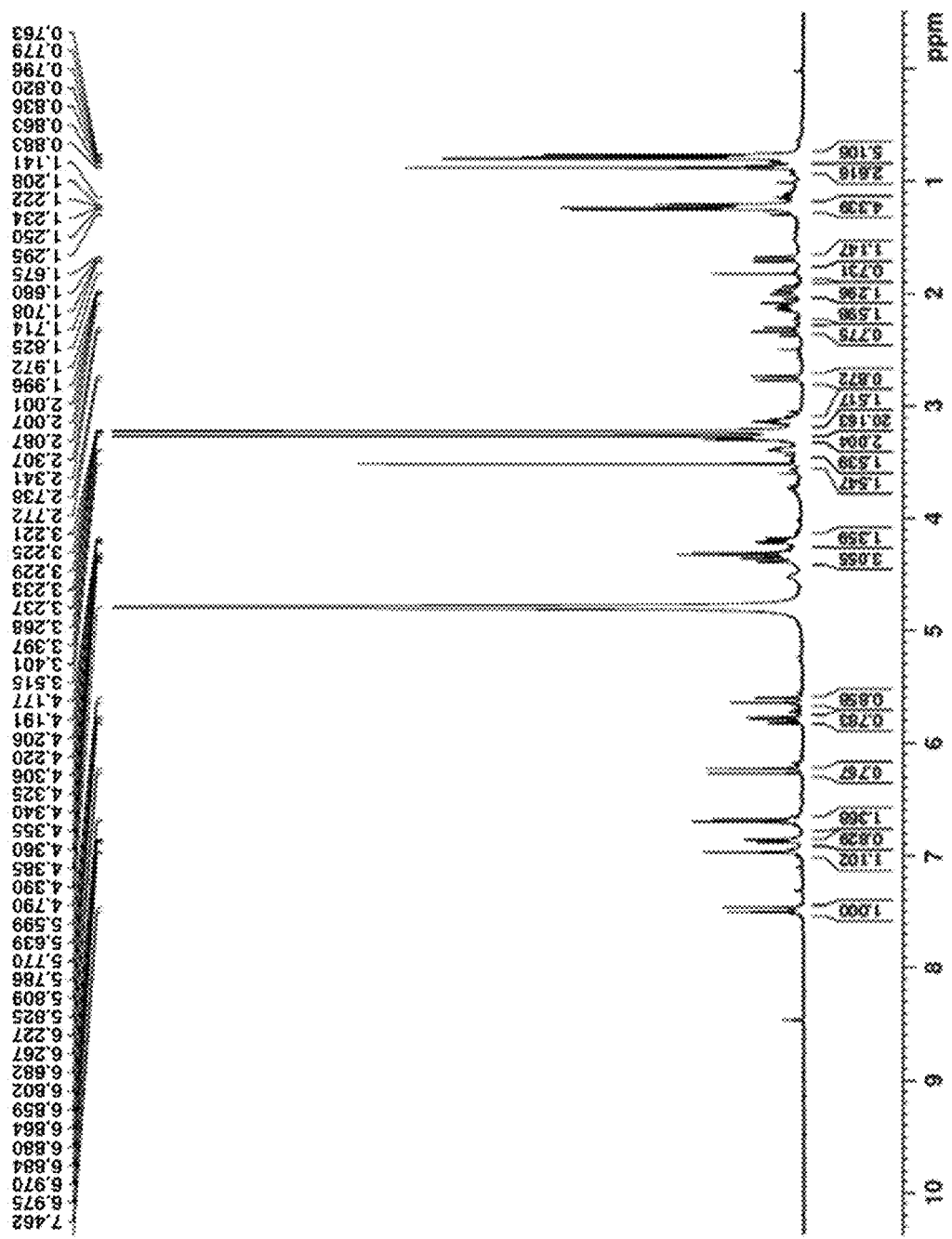
FIGS. 1A-1B respectively show the $^1$H NMR spectrum and $^{13}$C NMR spectrum of 6'-O-caffeoylampelopsisionoside (compound 1).

The present invention provides an *Aster glehni* extract, a fraction thereof and the active compounds isolated therefrom, which are remarkably effective in decreasing the serum uric acid level.

*Aster glehni* is a perennial plant in the family Asteraceae, which grows naturally in the mountains of Ulleungdo in Korea. It is similar to leopard plant in shape and grows up to about 1-1.5 m in height. It has fine hair at the stem and its rhizomes grow sideways. The leaves, which grow in alternation, are oblong with sharp ends. They have spots on the backside and have irregular teeth at the edge. The white flower blooms corymbosely at the end of the main stem in August or September. In Ulleungdo, this plant is called 'Bujiggaengi'. Young leaves and stems with strong flavor are harvested in early spring to be used for food.

At present, the antioxidant, antiinflammatory, anticonvulsant, sedative or sleep-inducing effects of *Aster glehni* have been known. Phenol-based compounds such as flavonoids and terpene compounds are known as its main ingredients.

The present invention provides novel compounds isolated from *Aster glehni*, which are effective in lowering the serum uric acid level.

The active compounds isolated from *Aster glehni* in the present invention are 6'-O-caffeoylampelopsisionoside (compound 1), 6'-O-caffeoylroseoside (compound 2), 6'-O-caffeoylsonchuinoside C (compound 3), 6'-O-caffeoyldihydrosyringin (compound 4) and glehnoside (compound 5), all of which are novel compounds.

Compound 1

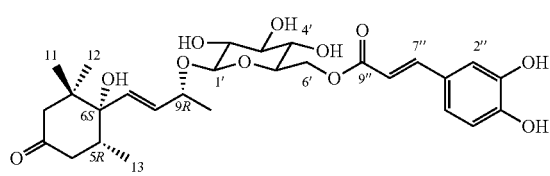

-continued

Compound 2

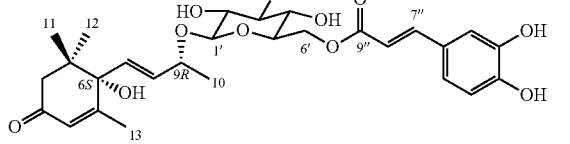

Compound 3

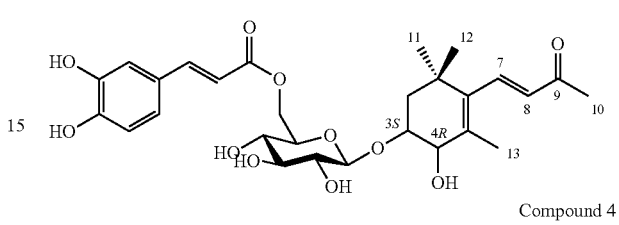

Compound 4

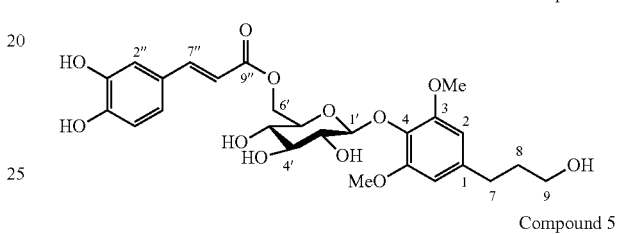

Compound 5

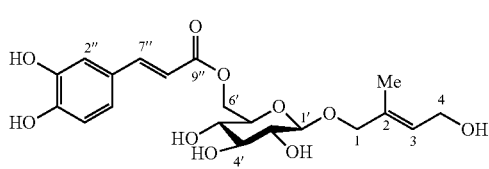

The present invention also provides a method for isolating the active compounds from *Aster glehni*.

The method for isolating the active compounds from *Aster glehni* includes:

1) obtaining a solvent extract by extracting the aerial part or underground part of *Aster glehni* with one or more extraction solvent selected from dichloromethane, acetone, an aqueous solution of acetone, a $C_{1-4}$ alcohol and an aqueous solution of a $C_{1-4}$ alcohol;

2) obtaining an ethyl acetate fraction by extracting the solvent extract with water and ethyl acetate; and 3) obtaining 6'-O-caffeoylampelopsisionoside (compound 1), 6'-O-caffeoylroseoside (compound 2), 6'-O-caffeoylsonchuinoside C (compound 3), 6'-O-caffeoyldihydrosyringin (compound 4) and glehnoside (compound 5) by subjecting the ethyl acetate fraction to column chromatography.

In the step 1) of obtaining the solvent extract, aerial part, underground part or whole plant of *Aster glehni* may be used. Specifically, the aerial part, such as leaf, flow or stem, of *Aster glehni* may be used. The harvested *Aster glehni* is used after drying in the shade. It may be used after being cut finely, powdered and, optionally, after being freeze-dried.

In the present invention, a commonly used organic solvent may be used as the extraction solvent. Specifically, one or more selected from dichloromethane, acetone, an aqueous solution of acetone, a $C_{1-4}$ alcohol and an aqueous solution of a $C_{1-4}$ alcohol may be used. More specifically, dichloromethane, acetone, methanol, butanol, a mixture solvent or an aqueous solution thereof containing 20-80 vol % of water may be used as the extraction solvent.

To describe the step 1) of obtaining the solvent extract more specifically, extraction is conducted by adding 0.1-5 L, specifically 0.5-1.0 L, of the extraction solvent per 1 kg of *Aster glehni* and keeping at room temperature for 4-5 days. The extraction may be performed 1-5 times, or more if necessary. The extraction temperature may be specifically 10-100° C., more specifically room temperature, although not being limited thereto. The extraction time may be specifically 1-7 days, more specifically 3-7 days, although not being limited thereto. The obtained extract is filtered, evaporated under reduced pressure and dried to obtain a solvent extract. Specifically, the evaporation under reduced pressure may be carried out using a rotary vacuum evaporator, although not being limited thereto. And, the drying method may be selected from drying under reduced pressure, vacuum drying, boiling drying, spray drying, room temperature drying, freeze-drying, etc., although not being limited thereto.

In the step 2) of obtaining the fraction, the obtained solvent extract is extracted with water and ethyl acetate to obtain an ethyl acetate fraction.

To describe more specifically, the ethyl acetate fraction may be obtained by adding 1-5 L, specifically 1.5-2.0 L, of water and 0.1-5 L, specifically 1.0-1.5 L, of ethyl acetate (EA) per 1 kg of the solvent extract and then extracting sufficiently.

Also, in the present invention, the step 1) of obtaining the solvent extract using the organic solvent may be omitted and the ethyl acetate extract may be obtained by directly extracting *Aster glehni* with ethyl acetate. However, to obtain the Active compound with higher purity, it is preferred that the ethyl acetate fraction is obtained following the step 1) of obtaining the solvent extract.

In the step 3) of obtaining the active compounds, the obtained ethyl acetate fraction is subjected to column chromatography.

The column chromatography may be performed using a column filled with the filler selected from a group consisting of silica gel, Sephadex, RP-18, polyamide, Toyopearl and XAD resin. However, the selection of the filler is not specially limited in the present invention. The column chromatography may be carried out several times using on adequately selected filler. Most specifically, the column chromatography may be conducted using an adequate combination of Sephadex, RP-18 and silica gel as the filler.

Through the column chromatography process, the 5 novel compounds 6'-O-caffeoylampelopsisionoside (compound 1), 6'-O-caffeoylroseoside (compound 2), 6'-O-caffeoylsonchuinoside C (compound 3), 6'-O-caffeoyldihydrosyringin (compound 4) and glehnoside (compound 5) may be isolated.

The present invention also provides a pharmaceutical composition and a health food composition for treating, preventing and improving hyperuricemia or gout, which contains an *Aster glehni* extract or fractions thereof as the active ingredients.

Since the *Aster glehni* extract or the fraction thereof contains the active compounds 1-5, it exhibits remarkable effect in treating, preventing and improving hyperuricemia or gout.

The present invention also provides a pharmaceutical composition and a health food composition for treating, preventing and improving hyperuricemia or gout, which contains one or more compound selected from a group consisting of 6'-O-caffeoylampelopsisionoside (compound 1), 6'-O-caffeoylroseoside (compound 2), 6'-O-caffeoylsonchuinoside C (compound 3), 6'-O-caffeoyldihydrosyringin (compound 4) and glehnoside (compound 5), which are isolated from an *Aster glehni* extract or a fraction thereof, or a pharmaceutically acceptable salt, hydrate or solvate thereof.

The present invention also provides a pharmaceutical composition and a health food composition for treating, preventing and improving hyperuricemia or gout, which contains one or more compound selected from a group consisting of 6'-O-caffeoylampelopsisionoside (compound 1), 6'-O-caffeoylroseoside (compound 2), 6'-O-caffeoylsonchuinoside C (compound 3), 6'-O-caffeoyldihydrosyringin (compound 4) and glehnoside (compound 5), which are synthesized via a common organic synthesis method, or a pharmaceutically acceptable salt, hydrate or solvate thereof.

The active compounds isolated from *Aster glehni* according to the present invention is chemically a megastigmane glycoside derivative, a hemiterpene glycoside derivative or a phenylpropanoid glycoside derivative and can be easily synthesized via a common organic synthesis method. Accordingly, the present invention also provides a pharmaceutical composition or a health food composition containing the compounds 1-5 as synthetic products, not as naturally occurring substances.

In the present invention, the pharmaceutically acceptable salt should have low toxicity in the human body and should not negatively affect the biological activity and physical and chemical properties of the parent compound. The salt may be prepared via a method commonly employed in this field and, specifically, may include a base addition salt formed from the addition of a base. The base may include an inorganic base such as alkali metal hydroxides (e.g., sodium hydroxide or or potassium hydroxide), alkali metal bicarbonates (e.g., sodium bicarbonate or potassium bicarbonate), alkali metal carbonates (e.g., sodium carbonate, potassium carbonate or calcium carbonate), etc. or an organic base such as primary, secondary and tertiary amines and amino acids. In addition to the pharmaceutically acceptable salt described above, a hydrate or a solvate may be used. In the present invention, the hydrate or the solvate may be prepared by dissolving the parent compound in a solvent and crystallizing or recrystallizing the same after adding a free acid or a free base. Also, the solvate (particularly, the hydrate) may be formed during the isolation of the compound of the present invention or with the passage of time due to absorption of water by the compound.

The *Aster glehni* extract, the fraction thereof or the active compounds isolated therefrom according to the present invention was found to have the activity of inhibiting production of uric acid by xanthine oxidase.

Accordingly, the *Aster glehni* extract, the fraction thereof or the active compound isolated therefrom may be contained in a pharmaceutical composition or a health food composition for treating, preventing and improving hyperuricemia or gout as the active ingredients. The gout that can be treated, prevented or improved by the composition of the present invention includes gouty arthritis, gouty renal disease and gouty nephrolithiasis, although not being limited thereto.

The pharmaceutical composition of the present invention may be administered orally or parenterally. For example, the pharmaceutical composition according to the present invention may be administered orally, intravenously, intramuscularly, intraartherially, intramedullarily, intradurally, intracardiacally, transdermally, subcutaneously, intraabdominally, intragastrically, sublingually or topically, although not being limited thereto.

For the clinical administration, the pharmaceutical composition of the present invention may be prepared into a suitable formulation using the known method. For example, for oral administration, it may be mixed with an inert diluent or an edible carrier, enclosed in a hard or soft gelatin capsule or compressed into a tablet for administration. For oral administration, the active compound may be prepared into an ingestible tablet, a buccal tablet, a troche, a capsule, an elixir, a suspension, a syrup, a wafer, etc. as being mixed with an excipient. Also, it may be prepared into various formulations for injection and parenteral administration using the method known or commonly employed in the art.

The pharmaceutical composition of the present invention may be usefully used to decrease uric acid level and prevent and treat gout. For example, the gout includes hyperuricemia, gouty arthritis, gouty renal disease, gouty nephrolithiasis, etc., although not being limited thereto.

The pharmaceutical composition of the present invention may be prepared into a medicinal formulation suitable for oral or parenteral administration by further containing an adequate carrier, excipient and/or diluent commonly used for preparation of drugs. In addition, a pharmaceutical formulation may be prepared using the pharmaceutical composition of the present invention according to a commonly employed method. When preparing the formulation, the active ingredient may be mixed with a carrier, diluted with a carrier or enclosed in a carrier in the form of capsule, cachet or other container. Accordingly, the formulation may be in the form of tablet, pill, powder, capsule, cachet, elixir, suspension, emulsion, liquid, syrup, aerosol, soft or hard gelatin capsule, solution or suspension for injection, ointment, cream, gel, lotion, etc.

A suitable carrier, excipient or diluent that can be contained in the pharmaceutical composition of the present invention may be, for example, lactose, dextrose, sucrose, sorbitol, mannitol, calcium silicate, cellulose, methyl cellulose, microcrystalline cellulose, polyvinylpyrrolidone, water, methyl hydroxybenzoate, propyl hydroxybenzoate, talc, magnesium stearate and mineral oil. The composition can additionally contain a commonly used filler, antiaggregant, lubricant, wetting agent, fragrance, emulsifier, preservative, etc. The composition of the present invention may be formulated by a method well known in the art so as to provide quick, sustained or controlled release of the active ingredient after being administered into a mammal.

The pharmaceutical composition according to the present invention may be administered, for example, orally, intravenously, intramuscularly, intraarterially, intramedullarily, intradurally, intracardiacally, transdermally, subcutaneously, intraabdominally, intragastrically, sublingually or topically, although not being limited thereto.

The administration dosage of pharmaceutical composition of the present invention will vary depending on the physical condition and body weight of a patient, the severity of disease, the type of drug and the route and period of administration and may be selected adequately by those skilled in the art. For the compounds 1-3, the administration dosage may be 0.001-500 mg/kg, specifically 0.001-200 mg/kg, based on the body weight of the patient. The administration may be made once or several times a day. However, the administration dosage does not restrict the scope of the present invention by any means.

The health food composition of the present invention contains the *Aster glehni* extract, the fraction thereof or the active compound isolated therefrom and is not particularly limited in type. For example, it may be in the form of drink, meat, sausage, bread, biscuit, cake, powdered grain, chocolate, candy, snack, confectionery, pizza, ramen, other noodles, gum, dairy products including ice cream, soup, beverage, alcoholic beverage, vitamin complex, milk and milk products, etc. and any functional health food in conventional sense is included.

The *Aster glehni* extract, the fraction thereof or the active compound isolated therefrom as the active ingredient may be added to food as it is or used together with food ingredients according to a commonly employed method. The effective content can be determined adequately depending on the purpose of use (prevention or improvement). Specifically, the active ingredient may be included in an amount of 0.001-70 wt % based on the total weight of the health food. However, when the health food composition is to be consumed for a long period of time the purpose of improvement of health and hygiene, the content may be less than the above range. Also, since it has no problem in terms of safety, the content of the active ingredient may be more than the above range.

For example, a health drink composition may contain, in addition to the active ingredient, natural carbohydrates, sweeteners, etc. as additives commonly used in ordinary drinks. Examples of the natural carbohydrate may include common sugars such as monosaccharides (e.g., glucose, fructose, etc.), disaccharides (e.g., maltose, sucrose, etc.) and polysaccharides (e.g., dextrin, cyclodextrin, etc.) and sugar alcohols such as xylitol, sorbitol, erythritol, etc. The natural carbohydrate may be contained in an amount of 1-20 wt %, specifically 5-10 wt %, based on the total weight of the health food composition. The sweetener may be either a natural sweetener (thaumatin, stevia extract, rebaudioside A, glycyrrhizin, etc.) or a synthetic sweetener (saccharin, aspartame, etc.). In addition, various nutrients, vitamins, minerals (electrolytes), flavors (synthetic or natural flavor), colorants, pectic acid and salts thereof, alginic acid and salts thereof, organic acids, protective colloidal thickeners, pH controlling agents, stabilizers, preservatives, glycerin, alcohols, carbonating agents used for carbonated drinks, etc. may be contained in the composition. Moreover, the composition may contain fruit pulp used in preparing natural fruit juices, fruit juice drinks and vegetable drinks. Although the content of the additives is not specially limited, they can be contained in an amount of 0.1-20 wt % based on the total weight of the health food composition.

EXAMPLES

The present invention will be described in more detail through examples and test examples. The following examples and test examples are for illustrative purposes only and it will be apparent to those skilled in the art not that the scope of this invention is not limited by the examples and test examples.

Examples

Example 1

Preparation of Extract or Fraction from Aerial Part of *Aster glehni*

The aerial part of *Aster glehni* (dry weight: 2.7 kg) harvested in Ulleungdo was extracted at room temperature for 4 days after adding 12 L of methanol. After repeating this procedure 3 times, followed by filtration and drying by concentration at 40° C. using a rotary evaporator, 394.8 g of a methanol extract was obtained. The methanol extract was suspended by adding 4000 mL of water and then extracted with dichloromethane ($CH_2Cl_2$, 4000 mL×3). The water layer was extracted with ethyl acetate (EtOAc, 4000 mL×3) to obtain an ethyl acetate fraction. Then, the water layer was extracted again with butanol (BuOH, 4000 mL×3) to obtain a butanol fraction.

Example 2

Preparation of Extract or Fraction from Underground Part of *Aster glehni*

The underground part of *Aster glehni* (dry weight: 1.03 kg) harvested in Ulleungdo was extracted at room temperature for 4 days after adding 10 L of methanol. After repeating this procedure 3 times, followed by filtration and drying by concentration at 40° C. using a rotary evaporator, 138.2 g of a methanol extract was obtained. The methanol extract was suspended by adding 1300 mL of water and then extracted with dichloromethane ($CH_2Cl_2$, 1300 mL×3). The water layer was extracted with ethyl acetate (EtOAc, 4000 mL×3) to obtain an ethyl acetate fraction. Then, the water layer was extracted again with butanol (BuOH, 4000 mL×3) to obtain a butanol fraction.

Example 3

Isolation of Novel Compounds from Ethyl Acetate Fraction 14.6 g of the ethyl acetate fraction from the aerial part of *Aster glehni* obtained in Example 1 was subjected to column chromatography using a Sephadex column (5×45 cm). Methanol was used as an eluent. The resulting fractions were observed by normal phase silica gel TLC (eluent: dichloromethane/methanol/water=30/10/1) and divided into 9 subfractions (EA-EI) based on the polarity of the compounds. The subfraction EC (1.4 g) was divided into 9 subfractions (EC1-EC9) by Sephadex column chromatography using 70% methanol as an eluent. The subfraction EC3 (385.7 mg) was subjected to column chromatography using reverse phase silica gel as a stationary phase and using 45% methanol as an eluent. It was divided into 20 subfractions (EC31-EC320) by TLC.

6'-O-Caffeoylampelopsisionoside (compound 1) (4.4 mg) was isolated from the subfraction EC310 (23.4 mg) by repeating normal phase silica gel and preparative reverse phase TLC (40% methanol) for purification.

The subfraction EC34 (614.4 mg) was subjected to column chromatography using reverse phase silica gel. 45% methanol was used as an eluent and the polarity was gradually increased to 100% methanol. 35 subfractions (EC34-1-EC34-35) were obtained. The second subfraction EC34-2 (68.2 mg) was subjected to column chromatography using normal phase silica gel and preparative reverse phase TLC (50% methanol) for fractionation. As a result, glehnoside (compound 5) (7.1 mg) was isolated.

The third subfraction EC34-3 (70.3 mg) was subjected to column chromatography using normal phase silica gel and preparative reverse phase TLC (48% methanol) and Toyopearl HW-40 (methanol) for fractionation. As a result, 6'-O-caffeoyldihydrosyringin (compound 4) (8.7 mg) and glehnoside (compound 5) (15.6 mg) were isolated.

The fourth subfraction EC34-4 (54.8 mg) was subjected to column chromatography using normal phase silica gel and preparative reverse phase TLC (50% methanol) for fractionation. As a result, 6'-O-caffeoyldihydrosyringin (compound 4) (3.3 mg) was isolated.

The fifth subfraction EC34-5 (112.1 mg) was repeatedly subjected to column chromatography using normal phase silica gel and reverse phase TLC (50% methanol) and finally subjected to column chromatography using reverse phase TLC for fractionation and using a Sephadex column. As a result, 6'-O-caffeoyldihydrosyringin (compound 4) (11.8 mg) was isolated.

The sixth subfraction EC34-6 (54.4 mg) was repeatedly subjected to column chromatography using normal phase silica gel and reverse phase TLC (50% methanol) and finally subjected to column chromatography using reverse phase TLC for fractionation and using a Sephadex column. As a result, 6'-O-caffeoylroseoside (compound 2) (5.7 mg) and 6'-O-caffeoylsonchuinoside C (compound 3) (9.2 mg) were isolated.

Example 4

Structural Characterization of Novel Compounds

The optical rotations $[\alpha]_D$ of the novel compounds isolated from the ethyl acetate fraction of the aerial part of *Aster glehni* were measured in a methanol solution and 400 MHz ($^1$H) and 100 MHz ($^{13}$C) spectra were recorded. The chemical shifts of each peak were presented relative to trimethylsilane as internal standard. The 1H NMR and $^{13}$C NMR spectra of the compounds are shown in FIGS. 1-5.

(1) Structural Characterization of Compound 1
6'-O-caffeoylampelopsisionoside

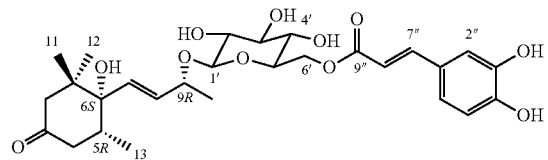

The chemical properties of the compound 1 are as follows.

Amorphous powder; $[\alpha]^{20}_D$ −9.4° (c 0.4, MeOH).

HR-ESI-TOP-MS (positive-ion mode) m/z 573.2311 [M+Na]$^+$ (calcd. for 573.2312, $C_{28}H_{38}O_{11}Na$).

Figure 1B:
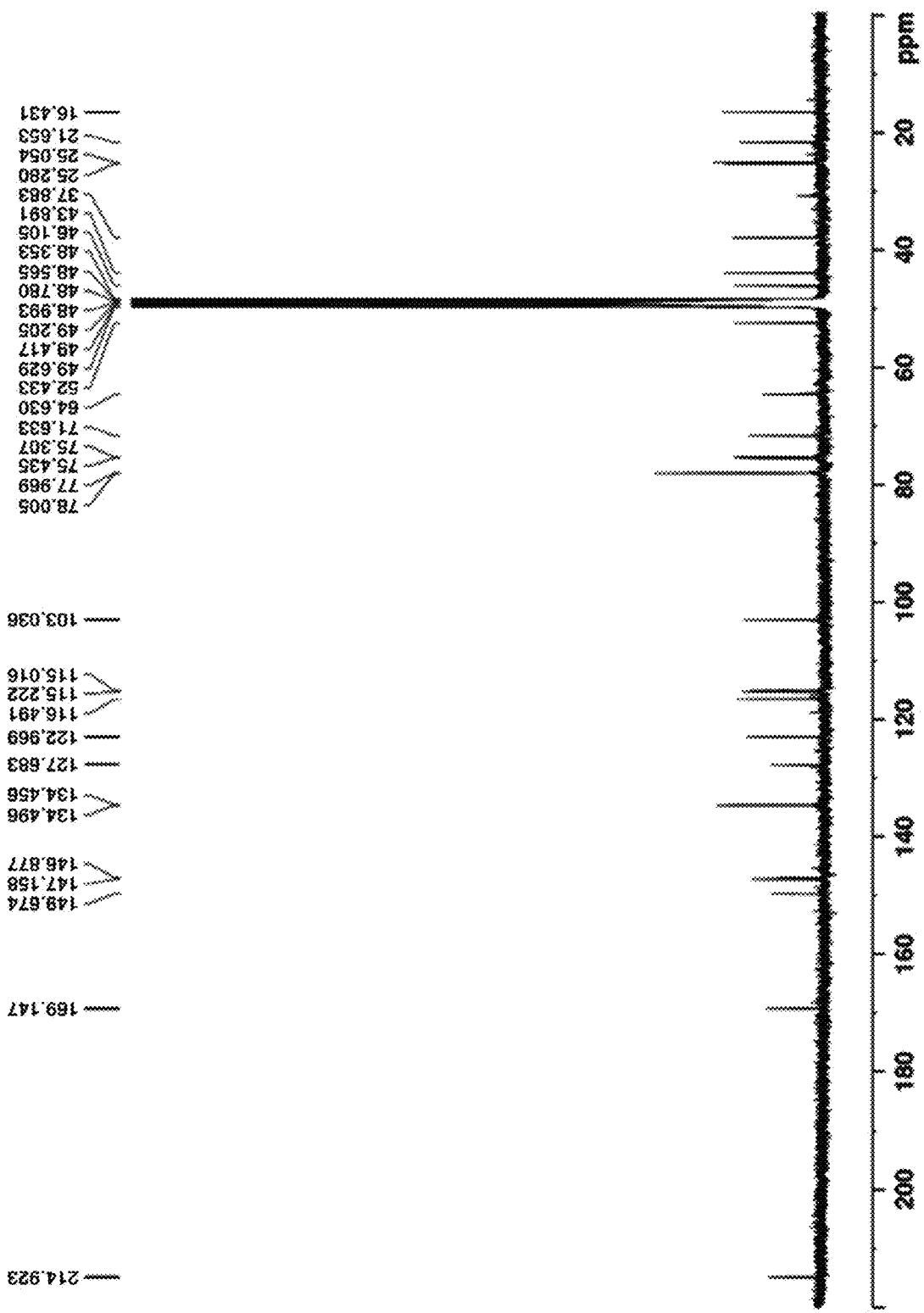

$^1$H (400 MHz) and $^{13}$C (100 MHz) NMR: see Tables 1-2 and FIG. 1.

This compound was identified as 6'-O-caffeoylampelopsisionoside by comparison with data described in the literatures (Marino et al., *J. Agric. Food Chem.*, 2004, 52, 7525; Inada et al., *Chem. Pharm. Bull.* 1991, 39, 2437). It is a novel compound that has never been reported.

(2) Structural Characterization of Compound 2
6'-O-Caffeoylroseoside

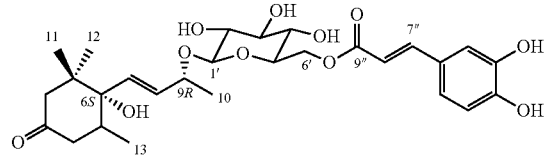

The chemical properties of the compound 2 are as follows.

Amorphous powder; $[\alpha]^{21}_D$ +42.8° (c 0.5, MeOH).

HR-ESI-TOP-MS (positive-ion mode) m/z 571.2159 [M+Na]$^+$ (calcd. for 571.2155, $C_{28}H_{36}O_{11}Na$).

Figure 2A:
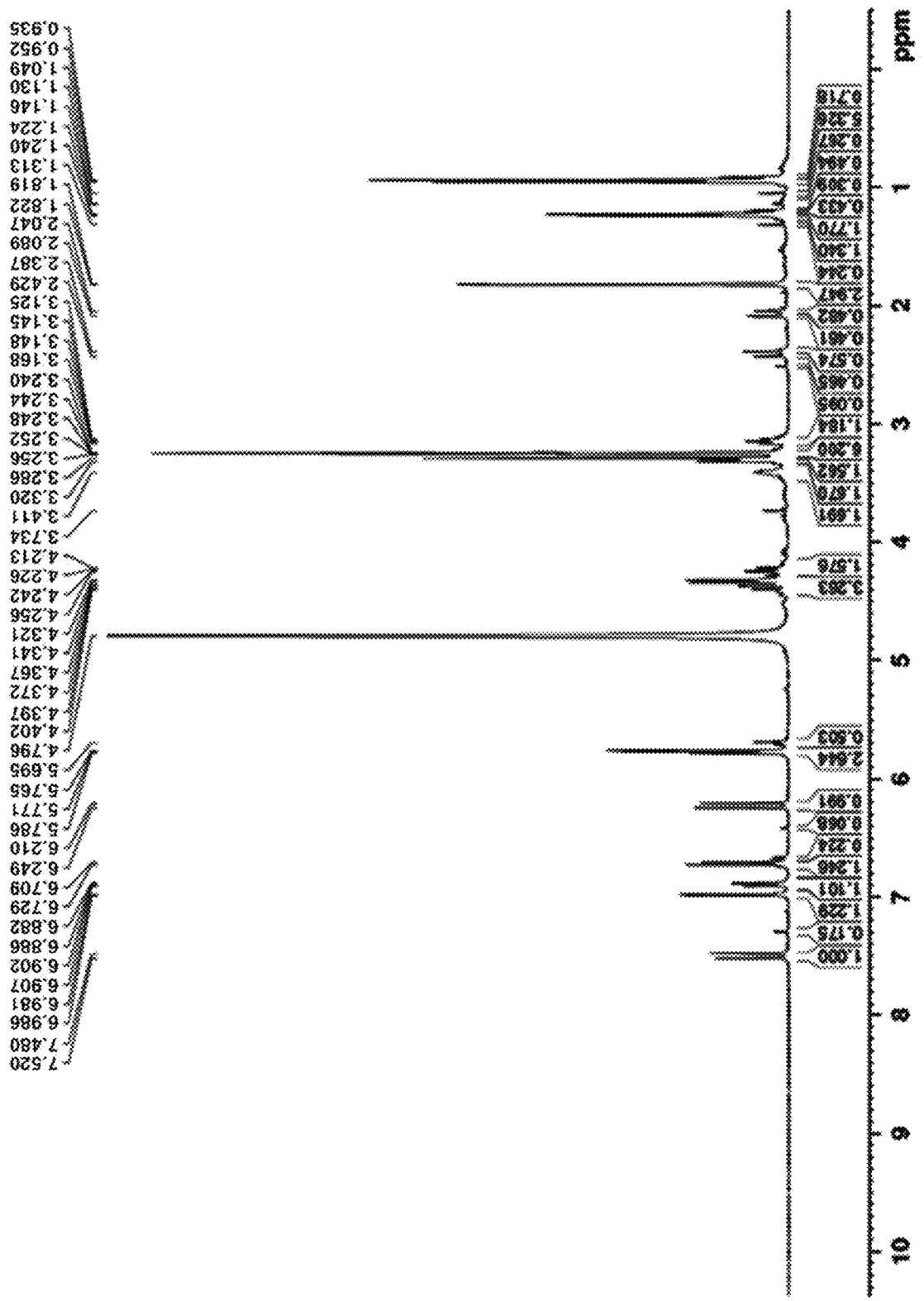
FIGS. 2A-2B respectively show the $^1$H NMR spectrum and $^{13}$C NMR spectrum of 6'-O-caffeoylroseoside (compound 2).
Figure 2B:
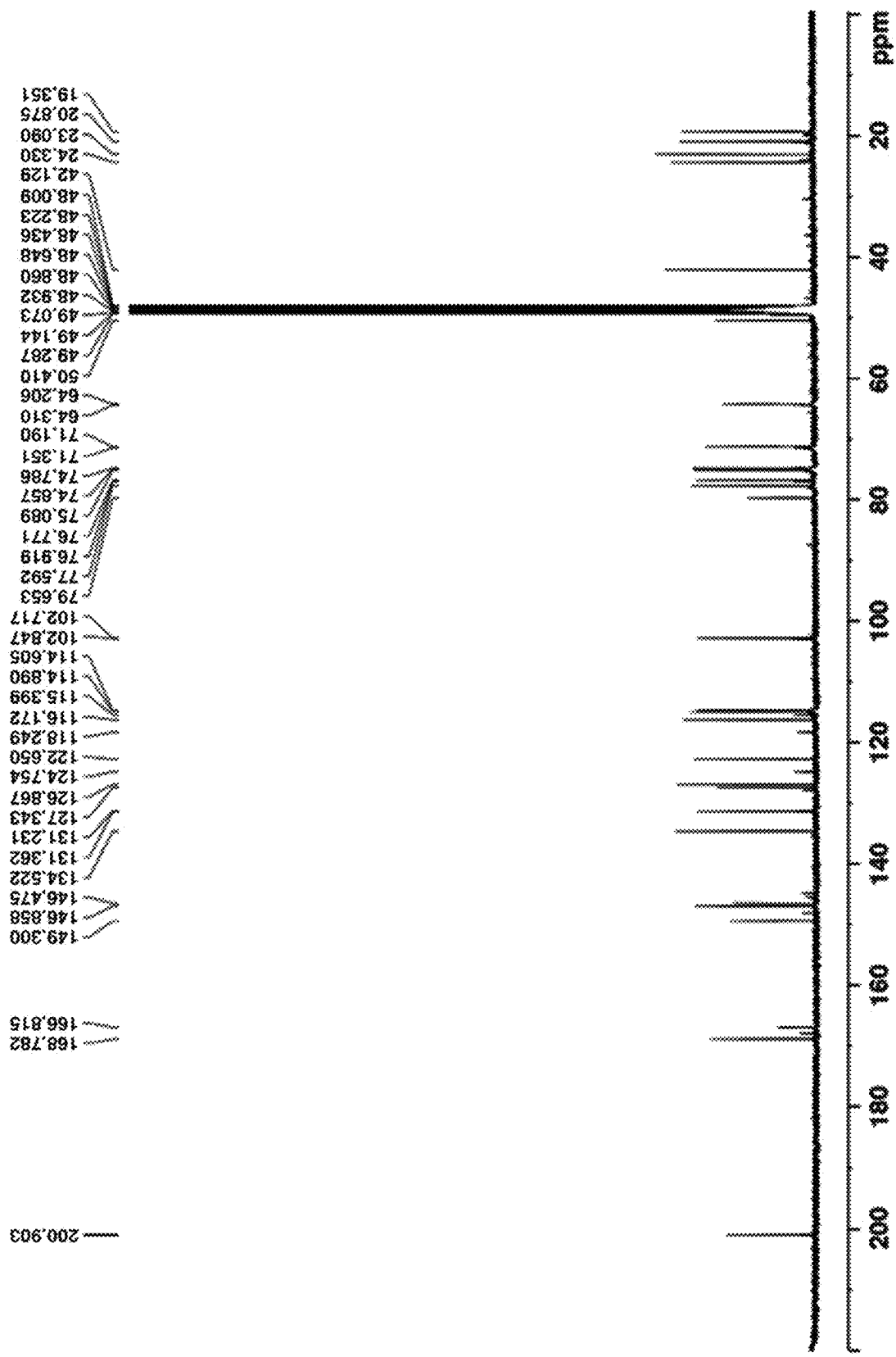
Figure 3A:
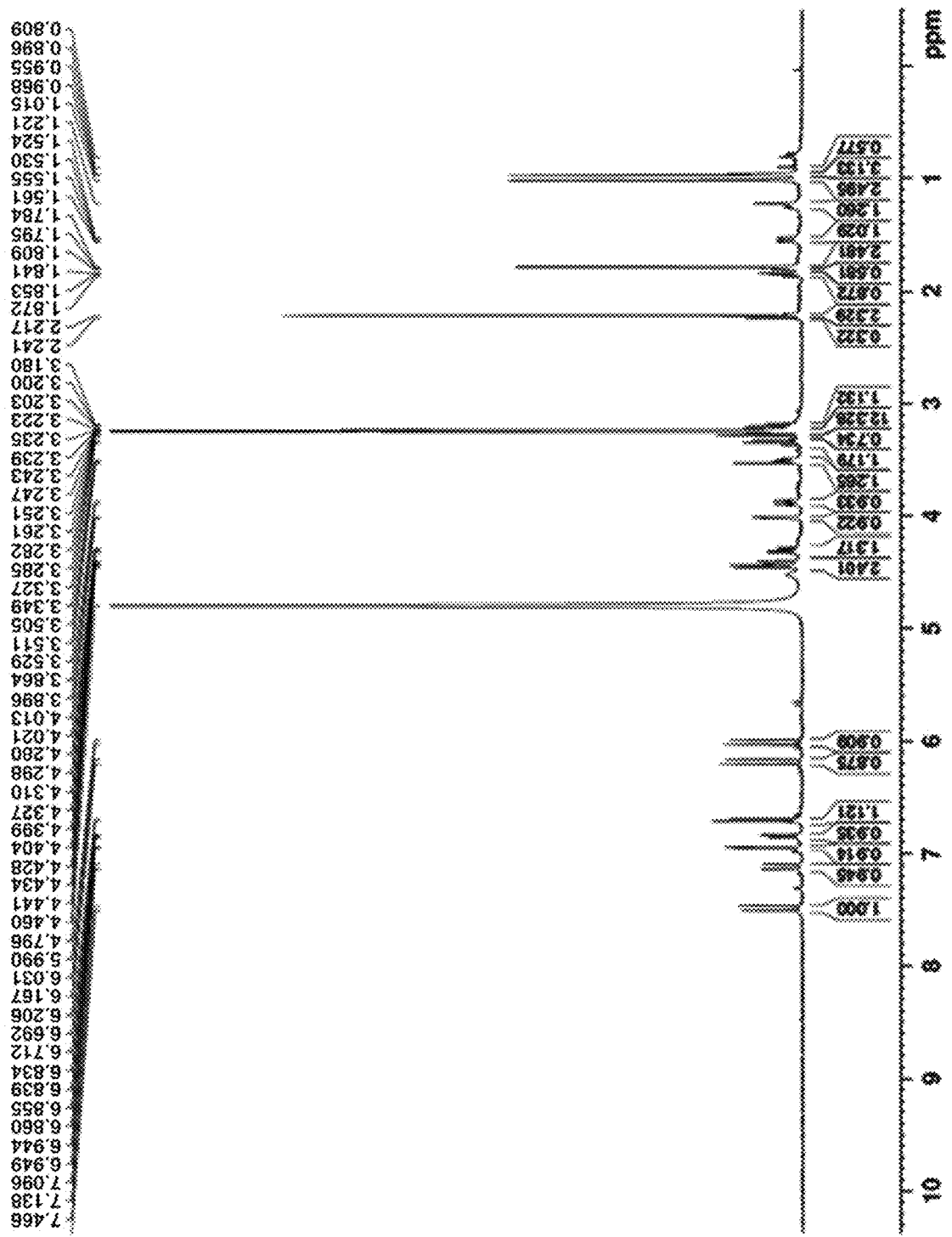
FIGS. 3A-3B respectively show the $^1$H NMR spectrum and $^{13}$C NMR spectrum of 6'-O-caffeoylsonchuinoside C (compound 3).
Figure 3B:
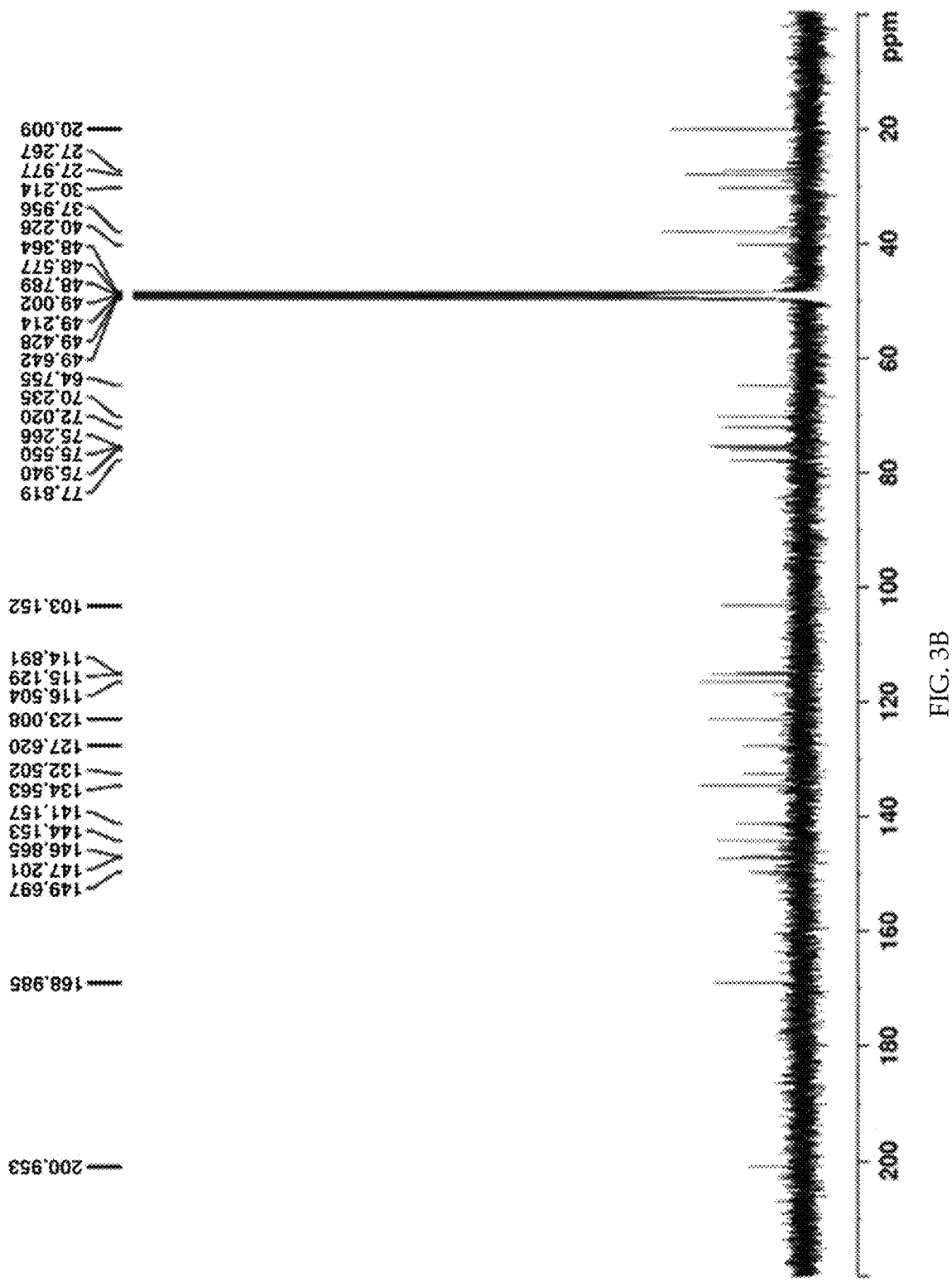
Figure 4A:
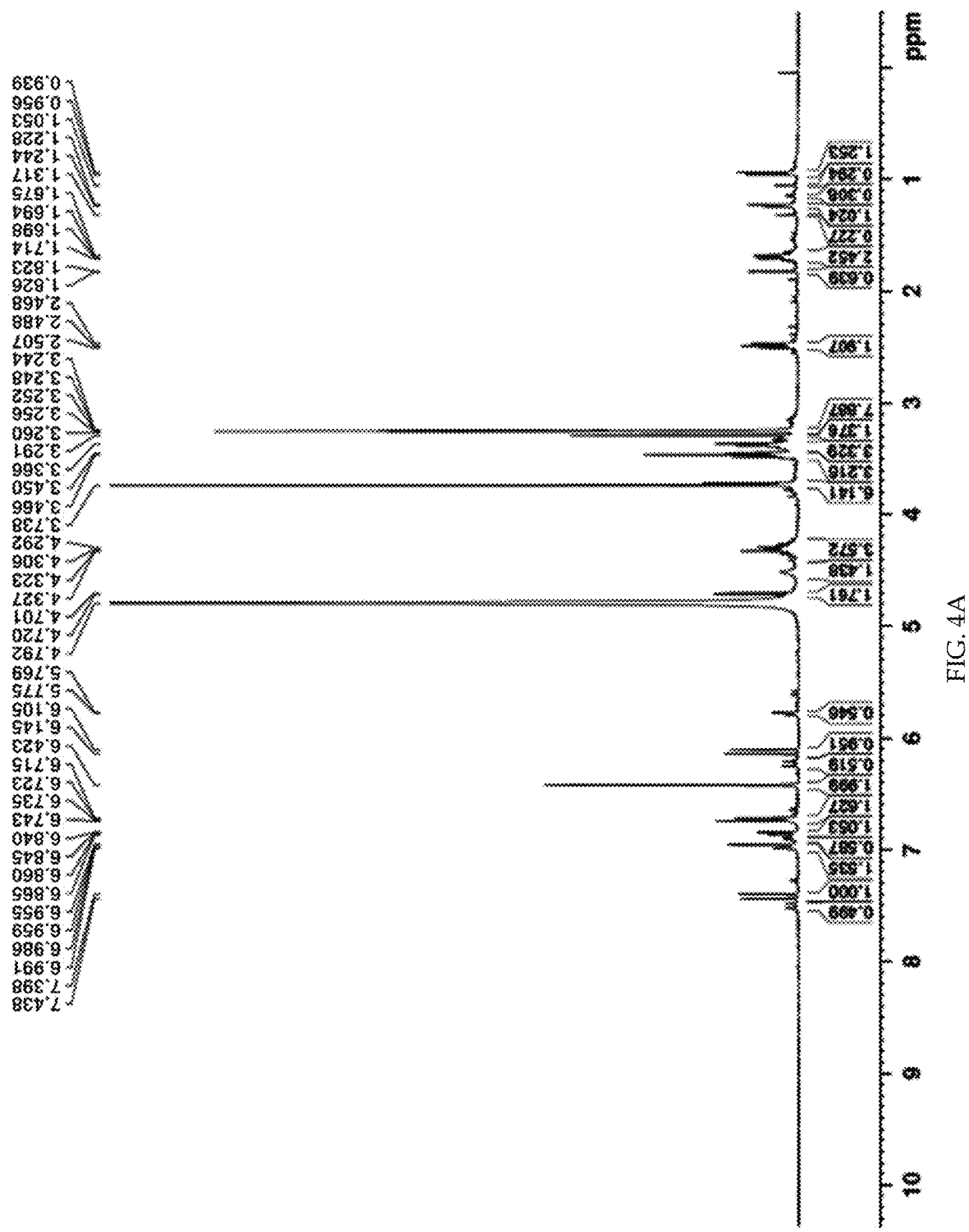
FIGS. 4A-4B respectively show the $^1$H NMR spectrum and $^{13}$C NMR spectrum of 6'-O-caffeoyldihydrosyringin (compound 4).
Figure 4B:
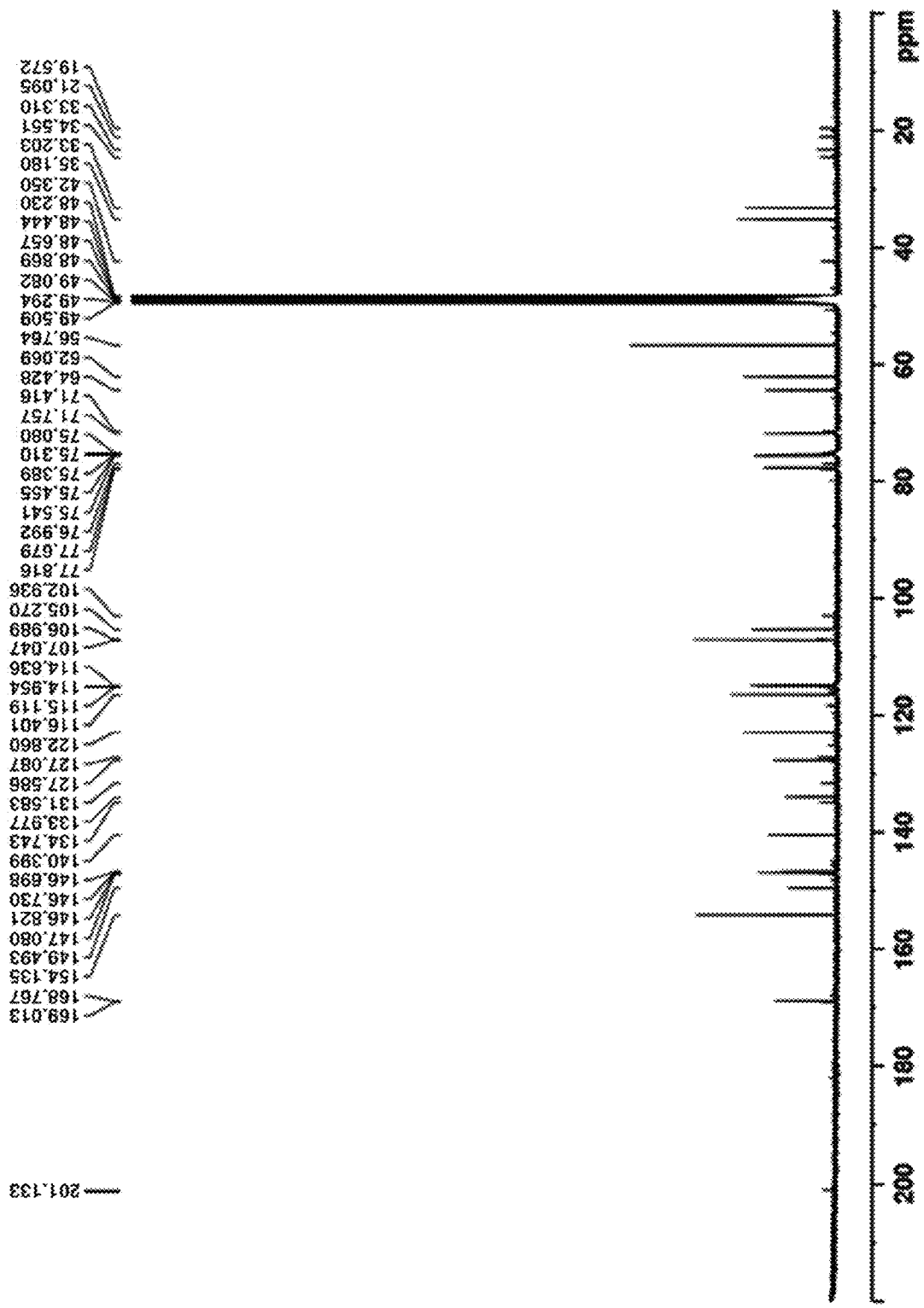
Figure 5A:
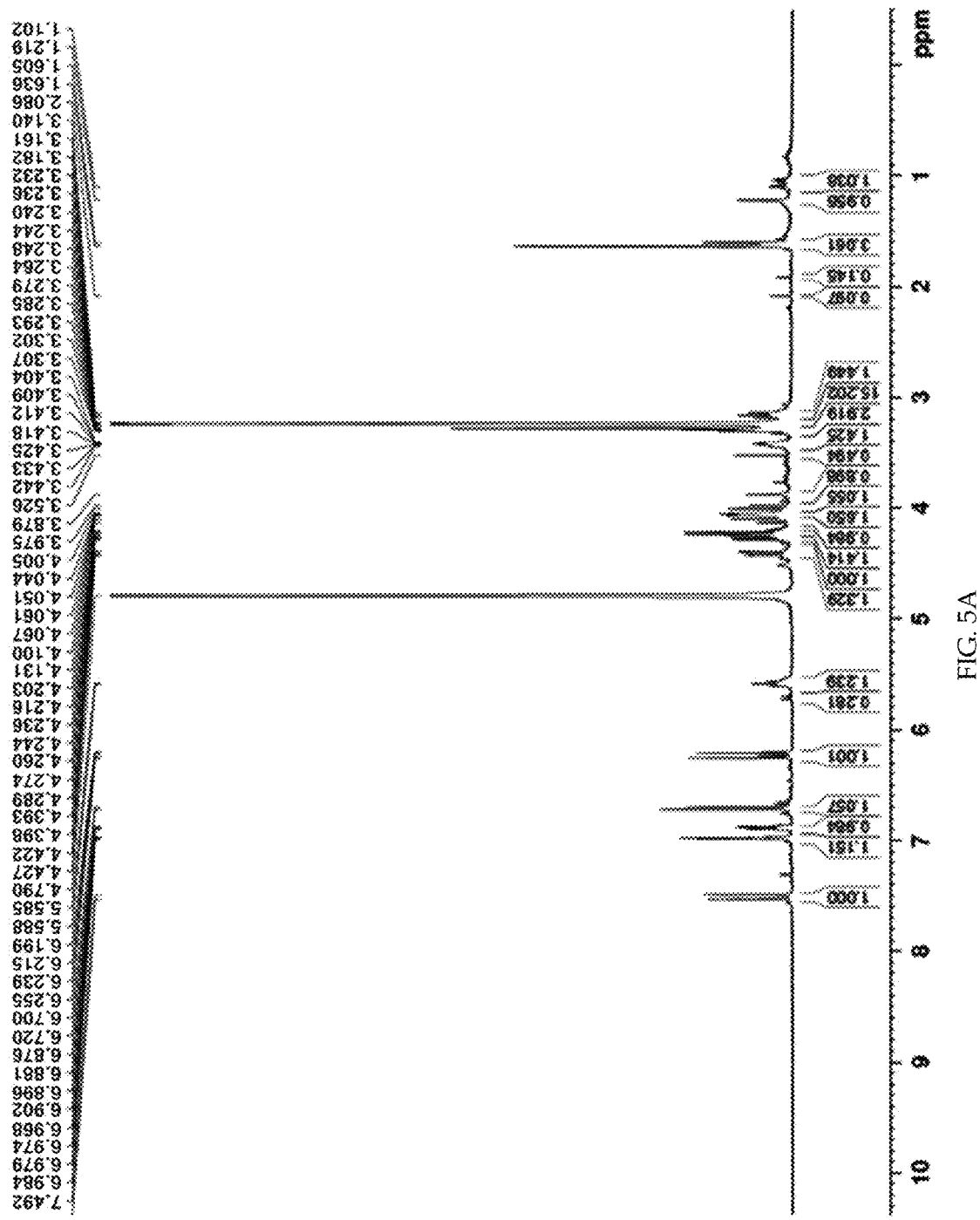
FIGS. 5A-5B respectively show the $^1$H NMR spectrum and $^{13}$C NMR spectrum of glehnoside (compound 5).
Figure 5B:
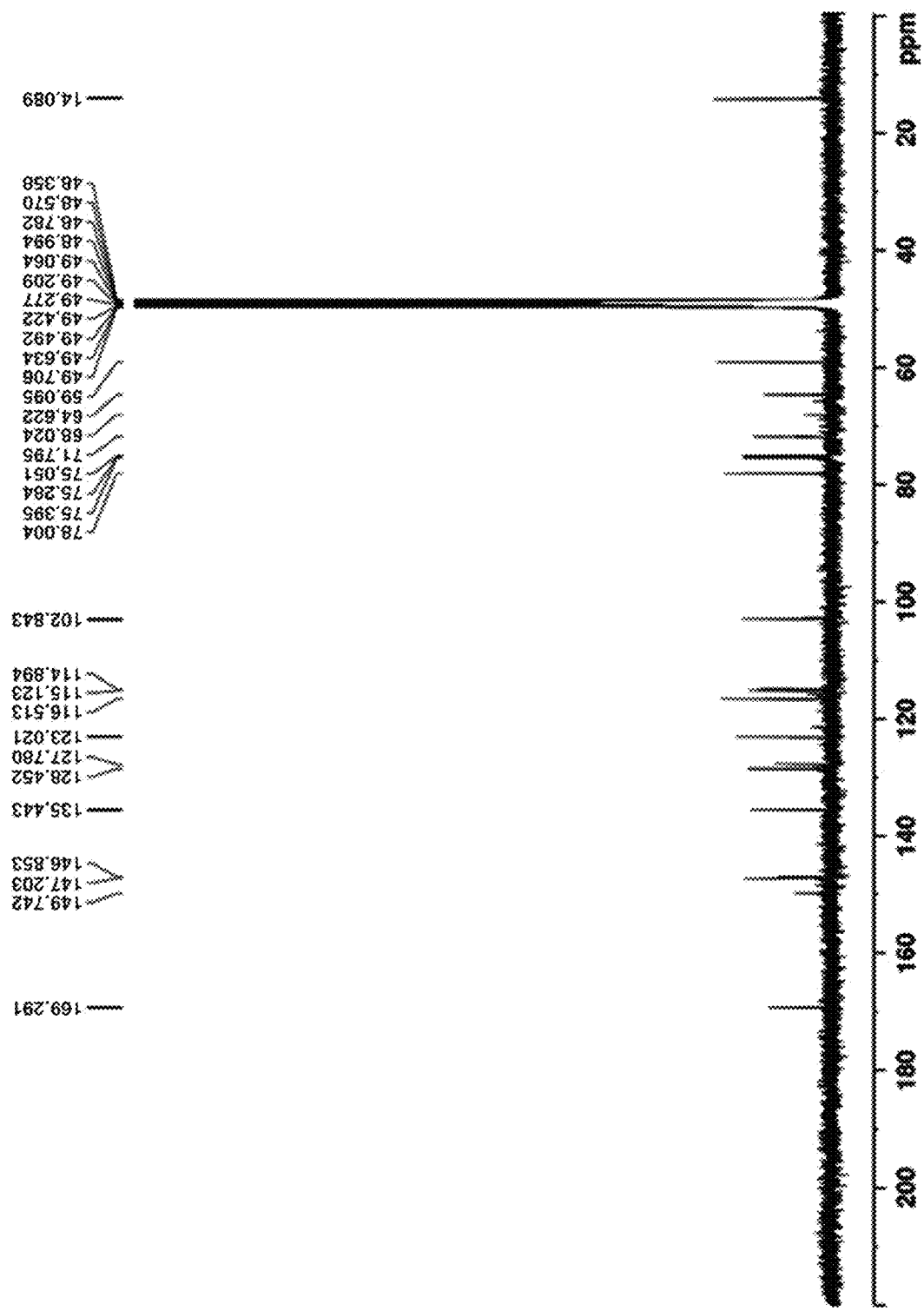

$^1$H (400 MHz) and $^{13}$C (100 MHz) NMR: see Tables 1-2 and FIG. 2.

This compound was identified as 6'-O-caffeoylroseoside by comparison with data described in the literatures (Otsuka et al., *Chem. Pharm. Bull.* 1995, 43, 754; Pabst et al., *Phytochemistry* 1992, 31, 1649; Yamano and Ito *Chem. Pharm. Bull.* 2005, 45, 541; Weiss et al., *J. Chem. Soc. Chem. Commun.* 1973, 565). It is a novel compound that has never been reported.

(3) Structural Characterization of Compound 3
6'-O-Caffeoylsonchuinoside C

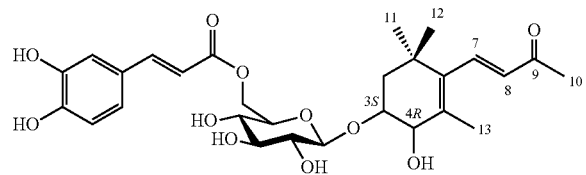

The chemical properties of the compound 3 are as follows.

Amorphous powder; $[\alpha]^{24}_D$ −35.6° (c 0.4, MeOH).
HR-ESI-TOP-MS (positive-ion mode) m/z 571.2160 [M+Na]$^+$ (calcd. for 571.2155, $C_{28}H_{36}O_{11}Na$).
$^1$H (400 MHz) and $^{13}$C (100 MHz) NMR: see Tables 1-2 and FIG. 3.

This compound was identified as 6'-O-caffeoylsonchuinoside C by comparison with data described in the literatures (Uchiyama et al., *Phytochemistry* 1990, 29, 2947; Lee et al., *Chem. Pharm. Bull.*, 2011, 59, 773). It is a novel compound that has never been reported.

(4) Structural Characterization of Compound 4
6'-O-Caffeoyldihydrosyringin

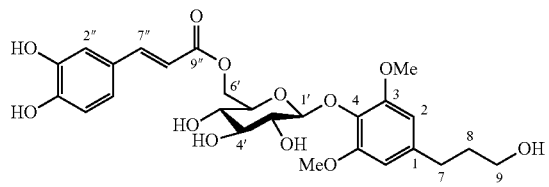

The chemical properties of the compound 4 are as follows.

Amorphous powder; $[\alpha]^{20}_D$ −51.2° (c 0.5, MeOH).
HR-ESI-TOP-MS (positive-ion mode) m/z 559.1793 [M+Na]$^+$ (calcd. for 559.1791, $C_{26}H_{32}O_{12}Na$).
$^1$H (400 MHz) and $^{13}$C (100 MHz) NMR: see Tables 1-2 and FIG. 4.

This compound was identified as 6'-O-caffeoyldihydrosyringin by comparison with data described in the literature (Wagner et al., *Planta Med.*, 1982, 44, 193). It is a novel compound that has never been reported.

(5) Structural Characterization of Compound 5
Glehnoside

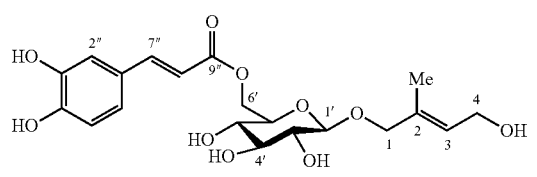

The chemical properties of the compound 5 are as follows.

Amorphous powder; $[\alpha]^{19}_D$ −26.2° (c 0.7, MeOH).
HR-ESI-TOP-MS (positive-ion mode) m/z 449.1422 [M+Na]$^+$ (calcd. for 449.1424, $C_{20}H_{26}O_{10}Na$).
$^1$H (400 MHz) and $^{13}$C (100 MHz) NMR: see Tables 1-2 and FIG. 5.

This compound was identified as (E)-2-methyl-but-2-enyl-6'-O-caffeoyl-β-glucopyranoside by comparison with data described in the literatures (Bohlmann et al., *Org. Mag. Res.*, 1975, 7, 426; Nicoletti et al., *Planta Med.*, 1992, 58, 472; Toyota et al., *Chem. Pharm. Bull.* 2002, 50, 508) and was named as glehnoside.

TABLE 1

| | $^1$H NMR (400 MHz, CD$_3$OD) Spectroscopic Data | | |
|---|---|---|---|
| H | Compound 1 | Compound 2 | Compound 3 |
| 2eq | 1.69 (dd, 2.4, 13.6) | 2.06 (d, 16.8) | 1.54 (dd, 2.4, 12.4) |
| 2ax | 2.75 (d, 13.6) | 2.40 (d, 16.8) | 1.82 (d, 12.8) |
| 3 | | | 3.86 (td, 3.6, 12.8) |
| 4eq | 1.98 (ddd, 2.0, 4.4, 14.0) | 5.78 br s | 4.01 (d, 3.2) |
| 4ax | 2.32 (t, 13.6) | | |
| 5 | 2.14 m | | |
| 7 | 5.61 (d, 16.0) | 5.77 (d, 2.4) | 7.11 (d, 16.8) |
| 8 | 5.79 (dd, 6.4, 15.6) | 5.77 (d, 2.4) | 6.01 (d, 16.4) |
| 9 | 4.34 (overlapped) | 4.33 (overlapped) | |
| 10 | 1.24 (d, 6.4) | 1.23 (d, 6.4) | 2.21 s |
| 11 | 0.796 s | 0.95 s | 1.01 s |
| 12 | 0.883 s | 0.93 s | 0.97 s |
| 13 | 0.77 (d, 6.4) | 1.81 (d, 1.2) | 1.78 s |
| 1' | 4.31 (d, 7.6) | 4.33 (d, 8.0) | 4.45 (d, 7.6) |
| 2' | 3.15 (dd, 7.8, 9.08) | 3.14 (dd, 8.0, 9.2) | 3.20 (dd, 8.0, 9.2) |
| 3' | 3.31 m | 3.28 m | 3.49 (t, 9.2) |
| 4' | 3.29 m | 3.25 m | 3.26 (overlapped) |
| 5' | 3.41 m | 3.41 m | 3.51 m |
| 6' | 4.19 (dd, 5.6, 11.6) | 4.23 (dd, 5.6, 12.0) | 4.30 (dd, 6.8, 12.0) |
| 6' | 4.37 (dd, 2.0, 12.0) | 4.38 (dd, 2.0, 12.0) | 4.41 (dd, 2.4, 12.0) |
| 2'' | 6.97 (d, 2.0) | 6.98 (d, 2.0) | 6.94 (d, 2.0) |
| 5'' | 6.69 (d, 8.0) | 6.71 (d, 8.0) | 6.70 (d, 8.0) |
| 6'' | 6.87 (dd, 2.0, 8.0) | 6.89 (dd, 2.0, 8.4) | 6.84 (dd, 2.0, 8.4) |
| 7'' | 7.48 (d, 15.6) | 7.50 (d, 16.0) | 7.48 (d, 16.0) |
| 8'' | 6.24 (d, 16.0) | 6.23 (d, 15.6) | 6.18 (d, 15.6) |

TABLE 2

| | $^{13}$C NMR (100 MHz, CD$_3$OD) Spectroscopic Data | | |
|---|---|---|---|
| C | Compound 1 | Compound 2 | Compound 3 |
| 1 | 43.9 | 42.1 | 37.9 |
| 2 | 52.4 | 50.4 | 40.2 |
| 3 | 214.9 | 200.9 | 75.9 |
| 4 | 46.1 | 126.9 | 70.2 |
| 5 | 37.9 | 166.8 | 132.5 |
| 6 | 78.0 | 79.7 | 141.2 |
| 7 | 134.5 | 131.4 | 144.2 |
| 8 | 134.5 | 134.5 | 134.6 |
| 9 | 78.0 | 76.8 | 200.9 |
| 10 | 21.7 | 20.9 | 27.3 |
| 11 | 25.0 | 23.1 | 27.9 |
| 12 | 25.3 | 24.3 | 30.2 |
| 13 | 16.4 | 19.4 | 20.0 |
| 1' | 103.0 | 102.7 | 103.2 |
| 2' | 75.3 | 74.9 | 75.3 |
| 3' | 77.9 | 77.6 | 77.8 |
| 4' | 71.6 | 71.2 | 72.0 |
| 5' | 75.4 | 75.1 | 75.6 |
| 6' | 64.3 | 64.2 | 64.8 |
| 1'' | 127.7 | 127.3 | 127.6 |
| 2'' | 115.2 | 114.9 | 115.1 |
| 3'' | 146.9 | 146.5 | 146.9 |
| 4'' | 149.7 | 149.3 | 149.7 |

TABLE 2-continued $^{13}$C NMR (100 MHz, CD$_3$OD) Spectroscopic Data

| C | Compound 1 | Compound 2 | Compound 3 |
|---|---|---|---|
| 5" | 116.5 | 116.2 | 116.5 |
| 6" | 122.9 | 122.7 | 123.0 |
| 7" | 147.2 | 146.9 | 147.2 |
| 8" | 114.9 | 114.6 | 114.9 |
| 9" | 169.2 | 168.9 | 168.9 |

TABLE 3

$^1$H (400 MHz, CD$_3$OD) and $^{13}$C (100 MHz, CD$_3$OD) NMR Spectroscopic Data

| | Compound 4 | | Compound 5 | |
|---|---|---|---|---|
| No. | $\delta_H$ | $\delta_C$ | $\delta_H$ | $\delta_C$ |
| 1 | | 140.4 | 4.12, 4.00 (each d, 12.0) | 75.1 |
| 2 | 6.43 s | 107.0 | | 135.4 |
| 3 | | 154.1 | 5.59 (t-like, 6.4) | 128.5 |
| 4 | | 133.9 | 4.06 (dd, 2.4, 6.4) | 59.1 |
| 5 | | 154.1 | 1.63 s | 14.1 |
| 6 | 6.43 s | 107.0 | | |
| 7 | 2.49 (dd, 7.6, 8.0) | 33.2 | | |
| 8 | 1.70 m | 35.2 | | |
| 9 | 3.45 (overlapped) | 62.1 | | |
| OMe | 3.74 | 56.8 | | |
| 1' | 4.71 (d, 7.6) | 105.3 | 4.24 (d, 7.6) | 102.8 |
| 2' | 3.45 (overlapped) | 75.5 | 3.17 (t, 8.4) | 75.4 |
| 3' | 3.67 m | 77.7 | 3.30 m | 78.0 |
| 4' | 3.67 m | 71.8 | 3.29 m | 71.8 |
| 5' | 3.67 m | 75.5 | 3.43 m | 75.3 |
| 6' | 4.27 (dd, 5.2, 11.2) | 64.4 | 4.27 (dd, 6.0, 11.6) | 64.6 |
| 6' | 4.38 (dd, 2.0, 12.4) | | 4.42 (dd, 2.0, 11.6) | |
| 1" | | 127.6 | | 127.8 |
| 2" | 6.96 (d, 2.0) | 114.9 | 6.98 (d, 2.0) | 115.1 |
| 3" | | 146.7 | | 146.9 |
| 4" | | 149.5 | | 149.7 |
| 5" | 6.73 (d, 8.0) | 116.4 | 6.71 (d, 8.4) | 116.5 |
| 6" | 6.85 (dd, 2.0, 8.4) | 122.9 | 6.88 (dd, 2.0, 8.0) | 123.0 |
| 7" | 7.42 (d, 16.0) | 146.8 | 7.51 (d, 16.0) | 147.2 |
| 8" | 6.13 (d, 16.0) | 114.8 | 6.23 (d, 16.0) | 114.9 |
| 9" | | 168.8 | | 169.3 |

Test Examples

Test Example 1

Effects of Inhibiting Production of Uric Acid by Xanthine/Xanthine Oxidase

Uric acid is produced from xanthine oxidation by xanthine oxidase. The effects of inhibiting production of uric acid by an *Aster glehni* extract, fractions thereof and active compounds isolated therefrom were evaluated by the Noro et al.'s method with some modification (Noro et al., *Chem. Pharm. Bull.*, 1983, 31, 3984).

Specifically, the sample and xanthine oxidase (0.024 units/mL) were mixed in 100 mM phosphate buffer (pH 7.5) and preincubated at 25° C. for 10 min. The reaction was initiated by the addition of 100 μM xanthine and incubation was further carried out at 25° C. for 30 min. The reaction was then stopped by adding 1 N HCl, and the absorbance was measured at 295 nm. The inhibition of uric acid production A (%) was calculated according to Equation 1. The results are given in Table 4.

$A(\%)$=(Absorbance of sample)/(Absorbance of control)×100      [Equation 1]

TABLE 4

| Tested substances | | Inhibition of uric acid production* (IC$_{50}$, μg/mL) |
|---|---|---|
| Extract/fractions of aerial part | Methanol extract | 93.2 ± 3.6 |
| | Dichloromethane fraction | 69.3 ± 3.3 |
| | Ethyl acetate fraction | 4.7 ± 0.1 |
| | Butanol fraction | 33.2 ± 2.4 |
| Extract/fractions of underground part | Dichloromethane fraction | 32.4 ± 0.4 |
| | Ethyl acetate fraction | 21.8 ± 1.1 |
| | Butanol fraction | 280.8 ± 8.6 |

| Tested substances | | Inhibition of uric acid production* (IC$_{50}$, μM) |
|---|---|---|
| Active compounds | Compound 1 | 93.0 ± 1.7 |
| | Compound 2 | 42.0 ± 1.4 |
| | Compound 3 | 73.2 ± 5.1 |
| | Compound 4 | 71.1 ± 3.9 |
| | Compound 5 | 80.0 ± 4.9 |
| Control | Allopurinol | 3.0 ± 0.3 |

*All data are expressed as mean ± SEM of triplicate experiments.

As seen from Table 4, the ethyl acetate fraction from the aerial part of *Aster glehni* showed the most potent inhibitory activity and the butanol fraction also showed significant inhibitory effect. In addition, it can be seen that the dichloromethane fraction or the ethyl acetate fraction from the underground part of *Aster glehni* also showed significant inhibitory effects.

Test Example 2

Effect of Decreasing Serum Uric Acid Level in a Gout-induced Animal Model

The antigout activity of the ethyl acetate fraction from the aerial part of *Aster glehni* was tested using a gout-induced animal model. After inducing hyperuricemia in test animals by administering potassium oxonate, which is an uricase inhibitor, the effect of reducing serum uric acid level by the administration of test substances was tested. As a positive control, allopurinol was also administered to the gout-induced model for comparison, which was the synthetic xanthine oxidase inhibitor.

As the test animals, male Sprague-Dawley rats weighing 200 g±20% were used. They were accustomed to the laboratory environment for a week while sufficiently supplying feed and water in a cage set to temperature 23±3° C., relative humidity 55±15%, ventilation 10-20 times/hr, lighting 12 hours (from 8 a.m. to 8 p.m.) and illuminance 150-300 lux before testing.

Figure 6:
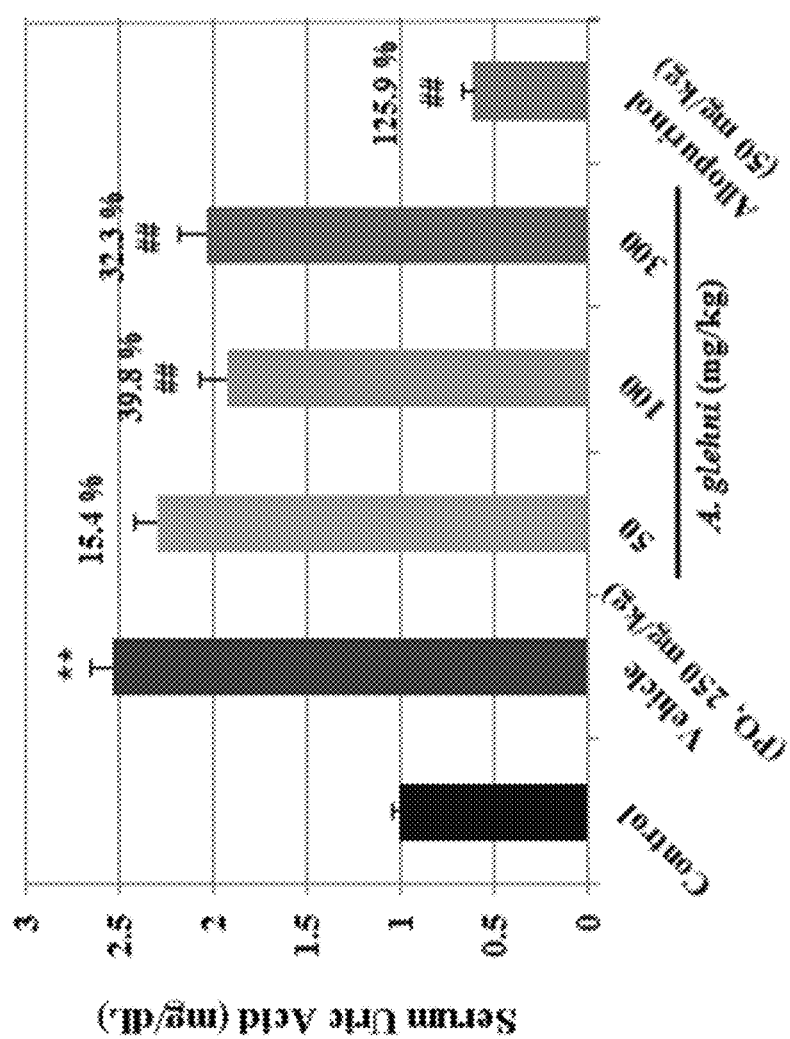
FIG. 6 shows decreases in the serum uric acid level in a gout-induced animal model after administration of an *Aster glehni* fraction.

The test animals were divided into four groups (normal control; hyperuricemia control (vehicle control); allopurinol-administered group (positive control); test substance-administered group) with 10 rats per each group. The allopurinol-administered group was supplemented with 50 mg/kg of allopurinol, and the test substance-administered group was orally supplemented with 50, 100 and 300 mg/kg of the test substance for 7 days, once a day. On the last day of administration (day 7), hyperuricemia was induced by intraperitoneally administering the uric acid oxidase inhibitor potassium oxonate (250 mg/kg). 1 hour later, the positive control substance or the test substance was orally administered. For the analysis of the uric acid level, blood was taken 2 hours after the administration on day 7 and the concentration of uric acid was measured. The result is shown in FIG. 6.

Statistical Analysis

One-way analysis of variance (ANOVA) was used assuming normality of data. When the ANOVA result was significant, the Newman-Keuls test was used as a post-hoc test to confirm significant difference between the non-induced vehicle control group (G1) and the induced vehicle control (G2), positive control (G3) and test substance-administered groups (G4, G5, G6).

TABLE 5

Test groups and administration dosage

| | Groups | Administered substances | Sex | n | Animal No. | Administered volume (mL/kg) | Administration dosage (mg/kg) |
|---|---|---|---|---|---|---|---|
| Non-induced | G1 | Vehicle[1] | M | 10 | 1-10 | 2 | — |
| Induced | G2 | Vehicle[1] | M | 10 | 11-20 | 2 | — |
| | G3 | Positive control (allopurinol) | M | 10 | 21-30 | 2 | 50 |
| | G4 | Test substance (low-dose) | M | 10 | 31-40 | 2 | 50 |
| | G5 | Test substance (medium-dose) | M | 10 | 41-50 | 2 | 100 |
| | G6 | Test substance (high-dose) | M | 10 | 51-60 | 2 | 300 |

[1]Vehicle: sterile water for injection

As seen from FIG. 6, the administration of the ethyl acetate fraction of *Aster glehni* resulted in reducing serum uric acid level as compared to the vehicle control group. Although the group administered with the ethyl acetate fraction of *Aster glehni* showed slightly lower ability of decreasing uric acid when compared with the allopurinol-administered group (positive control), it can be seen that the test substance, which is a safe natural product extracted from plant, can effectively replace the allopurinol with various side effects.

FORMULATION EXAMPLES

A pharmaceutical composition containing the *Aster glehni* extract, the fraction thereof or the active compound isolated therefrom according to the present invention can be prepared into various formulations depending on purposes. Formulation Examples 1-4 are described as exemplary formulations of drugs containing the extract, the fraction thereof or the active compounds isolated therefrom according to the present invention and the scope of the present invention is not limited thereby.

Formulation Example 1

Tablet (Direct Compression)

5.0 mg of the active ingredient was sieved, mixed with 14.1 mg of lactose, 0.8 mg of crospovidone USNF and 0.1 mg of magnesium stearate, and then compressed into a tablet.

Formulation Example 2

Tablet (Wet Granulation)

5.0 mg of the active ingredient was sieved and mixed with 16.0 mg of lactose and 4.0 mg of starch. Then, a solution of 0.3 mg of polysorbate 80 dissolved in pure water was added. After granulating and drying, the resulting granules were sieved, mixed with 2.7 mg of colloidal silicon dioxide and 2.0 mg of magnesium stearate, and then compressed into a tablet.

Formulation Example 3

Powder and Capsule 5.0 mg of the active ingredient was sieved and mixed with 14.8 mg of lactose, 10.0 mg of polyvinylpyrrolidone and 0.2 mg of magnesium stearate. The mixture was filled in a hard No. 5 gelatin capsule using a suitable apparatus.

Formulation Example 4

Injection

An injection was prepared from 100 mg of the active ingredient, 180 mg of mannitol, 26 mg of $Na_2HPO_4.12H_2O$ and 2974 mg of distilled water.

A health food composition containing the extract, the fraction thereof or the active compound isolated therefrom according to the present invention can be prepared into various formulations depending on purposes. Formulation Examples 5-9 are described as exemplary formulations of health functional foods containing the extract, the fraction thereof or the active compound isolated therefrom according to the present invention and the scope of the present invention is not limited thereby.

Formulation Example 5

Granular Health Food

A granular health food was prepared according to a commonly employed method by mixing 1000 mg of the active ingredient, 70 μg of vitamin A acetate, 1.0 mg of vitamin E, 0.13 mg of vitamin D, 0.15 mg of vitamin $B_2$, 0.5 mg of vitamin $B_6$, 0.2 μg of vitamin $B_{12}$, 10 mg of vitamin C, 10 μg of biotin, 1.7 mg of nicotinamide, 50 μg of folic acid, 0.5 mg of calcium pantothenate, 1.75 mg of ferrous sulfate, 0.82 mg of zinc oxide, 25.3 mg of magnesium carbonate, 15 mg of monopotassium phosphate, 55 mg of calcium phosphate, 90 mg of potassium citrate, 100 mg of calcium carbonate and 24.8 mg of magnesium chloride.

Formulation Example 6

Health Drink 1000 mg of the active ingredient was mixed with 1000 mg of citric acid, 100 g of an oligosaccharide, 2 g of a plum juice concentrate and 1 g of taurine and purified water was added to make the final volume 900 mL. After heating at 85° C. for about 1 hour under stirring, the resulting solution was filtered, bottled in a sterilized 2 L container, sealed and sterilized to prepare a health drink.

The mixing ratios described above as a specific example for a health drink can be varied as desired depending on local and ethnic preferences including class, country, purpose of use, etc.

Formulation Example 7

Flour Products

Bread, cake, cookie, cracker and noodles were prepared as health promoting foods using a mixture prepared by adding 0.5-5 g of the active ingredient to 100 g of wheat flour.

Formulation Example 8

Dairy Products

A variety of dairy products such as butter and ice cream were prepared using 100 g of milk to which 5-10 g of the active ingredient was added.

Formulation Example 9

Powdered Grain 30 g of brown rice, 20 g of barley, 10 g of glutinous rice and 15 g of adlay were gelatinized according to a known method, dried, roasted and then pulverized into 60-mesh powder. 7 g of black bean, 7 g of black sesame and 7 g of perilla seeds were steamed according to a known method, dried, roasted and then pulverized into 60-mesh powder. Powdered grain was prepared by mixing the grain powder and the seed powder with 3 g of the active ingredient.

As described above, the *Aster glehni* extract, the fraction thereof or the active compound isolated therefrom according to present invention has substantial effect of inhibiting the production of uric acid and decreasing the blood level of uric acid.

Accordingly, the *Aster glehni* extract, the fraction thereof or the active compounds isolated therefrom can be effectively used as an active ingredient of a drug or a health food for treating, preventing and improving hyperuricemia and gout, which are induced by the increased level of uric acid.

What is claimed is:

1. A method of treating hyperuricemia or gout comprising administering an effective amount of an *Aster glehni* extract to a mammal having hyperuricemia or gout.

2. The method according to claim 1, wherein the *Aster glehni* extract is obtained by extracting the aerial part or underground part of *Aster glehni* with one or more extraction solvent selected from dichloromethane, acetone, an aqueous solution of acetone, a $C_{1-4}$ alcohol and an aqueous solution of a $C_{1-4}$ alcohol.

3. A method of treating hyperuricemia or gout comprising administering an effective amount of an ethyl acetate fraction obtained by extracting an *Aster glehni* extract with ethyl acetate to a mammal having hyperuricemia or gout.

4. The method according to claim 3, wherein the *Aster glehni* extract or the ethyl acetate fraction comprises one or more compound selected from a group consisting of 6'-O-caffeoylampelopsisionoside, 6'-O-caffeoylroseoside, 6'-O-caffeoylsonchuinoside C, 6'-O-caffeoyldihydrosyringin and glehnoside.

5. The method according to claim 3, wherein the gout is a disease selected from a group consisting of gouty arthritis, gouty renal disease and gouty nephrolithiasis.

6. The method according to claim 1, wherein the *Aster glehni* extract comprises one or more compound selected from a group consisting of 6'-O-caffeoylampelopsisionoside, 6'-O-caffeoylroseoside, 6'-O-caffeoylsonchuinoside C, 6'-O-caffeoyldihydrosyringin and glehnoside.

7. The method according to claim 1, wherein the gout is a disease selected from a group consisting of gouty arthritis, gouty renal disease and gouty nephrolithiasis.

* * * * *